(12) United States Patent
Sherwood et al.

(10) Patent No.: US 9,129,749 B2
(45) Date of Patent: *Sep. 8, 2015

(54) SINTERED ELECTRODES TO STORE ENERGY IN AN IMPLANTABLE MEDICAL DEVICE

(75) Inventors: Gregory J. Sherwood, Shoreview, MN (US); Michael J. Root, Lino Lakes, MN (US); Peter Jay Kuhn, St. Paul, MN (US); Mary M. Byron, Roseville, MN (US); Eric Stemen, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 906 days.

This patent is subject to a terminal disclaimer.

(21) Appl. No.: 12/968,523

(22) Filed: Dec. 15, 2010

(65) Prior Publication Data

US 2011/0152958 A1    Jun. 23, 2011

Related U.S. Application Data

(60) Provisional application No. 61/288,062, filed on Dec. 18, 2009.

(51) Int. Cl.
*A61N 1/39* (2006.01)
*H01G 9/08* (2006.01)
(Continued)

(52) U.S. Cl.
CPC ............... *H01G 9/08* (2013.01); *H01G 9/008* (2013.01); *H01G 9/052* (2013.01); *H01G 9/06* (2013.01); *A61N 1/375* (2013.01); *A61N 1/3782* (2013.01); *Y10T 29/417* (2015.01)

(58) Field of Classification Search
CPC ......... H01G 9/008; H01G 9/10; H01G 9/052; H01G 9/042; H01G 9/045

USPC .................. 607/5; 361/508, 517, 520
See application file for complete search history.

(56) References Cited

U.S. PATENT DOCUMENTS

| 3,025,441 | A | 3/1962 | West |
| 3,331,759 | A | 7/1967 | Middelhoek et al. |

(Continued)

FOREIGN PATENT DOCUMENTS

| EP | 0877400 A1 | 11/1998 |
| EP | 1470267 B1 | 4/2009 |

(Continued)

OTHER PUBLICATIONS

Bocek, Joseph M, et al., "Method and Apparatus for Charging Partitioned Capacitors", U.S. Appl. No. 11/462,301, filed Aug. 3, 2006, 53 pgs.

(Continued)

*Primary Examiner* — Christopher D Koharski
*Assistant Examiner* — Jeremiah Kimball
(74) *Attorney, Agent, or Firm* — Schwegman Lundberg & Woessner, P.A.

(57) ABSTRACT

An example includes a capacitor case sealed to retain electrolyte, at least one anode disposed in the capacitor case, the at least one anode comprising a sintered portion disposed on a substrate, an anode conductor coupled to the substrate in electrical communication with the sintered portion, the anode conductor sealingly extending through the capacitor case to an anode terminal disposed on the exterior of the capacitor case with the anode terminal in electrical communication with the sintered portion, a cathode disposed in the capacitor case, a separator disposed between the cathode and the anode and a cathode terminal disposed on an exterior of the capacitor case and in electrical communication with the cathode, with the anode terminal and the cathode terminal electrically isolated from one another.

18 Claims, 9 Drawing Sheets

(51) Int. Cl.
*H01G 9/008* (2006.01)
*H01G 9/052* (2006.01)
*H01G 9/06* (2006.01)
*A61N 1/375* (2006.01)
*A61N 1/378* (2006.01)

(56) References Cited

U.S. PATENT DOCUMENTS

| | | | |
|---|---|---|---|
| 3,445,731 A | 5/1969 | Saeki et al. | |
| 3,627,520 A | 12/1971 | Rogers | |
| 3,638,083 A | 1/1972 | Dornfeld et al. | |
| 3,647,415 A | 3/1972 | Yano et al. | |
| 4,059,116 A | 11/1977 | Adams | |
| 4,085,397 A | 4/1978 | Yagher, Jr. | |
| 4,107,762 A | 8/1978 | Shirn et al. | |
| 4,406,286 A | 9/1983 | Stein | |
| 4,720,767 A | 1/1988 | Chan et al. | |
| 4,840,122 A | 6/1989 | Nerheim | |
| 4,882,115 A * | 11/1989 | Schmickl | 361/538 |
| 5,062,025 A | 10/1991 | Verhoeven et al. | |
| 5,115,378 A | 5/1992 | Tsuchiya et al. | |
| RE34,879 E | 3/1995 | Bocchi et al. | |
| 5,468,254 A | 11/1995 | Hahn et al. | |
| 5,591,211 A | 1/1997 | Meltzer | |
| 5,591,217 A | 1/1997 | Barreras | |
| 5,634,938 A | 6/1997 | Swanson et al. | |
| 5,660,737 A | 8/1997 | Elias et al. | |
| 5,763,911 A | 6/1998 | Matthews et al. | |
| 5,807,397 A | 9/1998 | Barreras | |
| 5,930,109 A | 7/1999 | Fishler | |
| 6,115,235 A | 9/2000 | Naito | |
| 6,141,205 A | 10/2000 | Nutzman et al. | |
| 6,161,040 A | 12/2000 | Blunsden | |
| 6,193,779 B1 | 2/2001 | Reichert et al. | |
| 6,241,751 B1 | 6/2001 | Morgan et al. | |
| 6,310,757 B1 | 10/2001 | Tuzuki et al. | |
| 6,347,032 B2 | 2/2002 | Naito | |
| 6,350,406 B1 | 2/2002 | Satou et al. | |
| 6,351,371 B1 * | 2/2002 | Yoshida et al. | 361/528 |
| 6,385,031 B1 | 5/2002 | Lerche et al. | |
| 6,456,877 B1 | 9/2002 | Fishler | |
| 6,459,566 B1 | 10/2002 | Casby et al. | |
| 6,493,212 B1 | 12/2002 | Clarke et al. | |
| 6,509,588 B1 | 1/2003 | O'Phelan et al. | |
| 6,560,089 B2 * | 5/2003 | Miltich et al. | 361/509 |
| 6,622,046 B2 | 9/2003 | Fraley et al. | |
| 6,678,559 B1 | 1/2004 | Breyen et al. | |
| 6,687,118 B1 | 2/2004 | O'Phelan et al. | |
| 6,699,265 B1 | 3/2004 | O'Phelan et al. | |
| 6,775,127 B2 | 8/2004 | Yoshida | |
| 6,778,860 B2 | 8/2004 | Ostroff et al. | |
| 6,785,123 B2 | 8/2004 | Keser | |
| 6,801,424 B1 * | 10/2004 | Nielsen et al. | 361/517 |
| 6,807,048 B1 | 10/2004 | Nielsen et al. | |
| 6,850,405 B1 * | 2/2005 | Mileham et al. | 361/302 |
| 6,855,234 B2 | 2/2005 | D'Astolfo, Jr. | |
| 6,865,417 B2 | 3/2005 | Rissmann et al. | |
| 6,914,769 B2 | 7/2005 | Welsch et al. | |
| 6,952,608 B2 | 10/2005 | Ostroff | |
| 6,954,670 B2 | 10/2005 | Ostroff | |
| 7,024,246 B2 | 4/2006 | Acosta et al. | |
| 7,327,557 B2 * | 2/2008 | Poplett | 361/520 |
| 7,342,774 B2 * | 3/2008 | Hossick-Schott et al. | 361/528 |
| 7,522,957 B2 | 4/2009 | Ostroff | |
| 7,531,010 B1 | 5/2009 | Feger et al. | |
| 7,564,677 B2 | 7/2009 | Poplett | |
| 7,760,488 B2 | 7/2010 | Breznova et al. | |
| 8,179,663 B2 | 5/2012 | Brabeck et al. | |
| 8,619,408 B2 | 12/2013 | Sherwood et al. | |
| 8,725,252 B2 | 5/2014 | Sherwood | |
| 8,873,220 B2 | 10/2014 | Sherwood et al. | |
| 2003/0169560 A1 | 9/2003 | Welsch et al. | |
| 2004/0019268 A1 | 1/2004 | Schmidt et al. | |
| 2004/0147960 A1 * | 7/2004 | O'Phelan et al. | 607/1 |
| 2004/0147961 A1 | 7/2004 | O'Phelan et al. | |
| 2004/0240155 A1 | 12/2004 | Miltich et al. | |
| 2005/0017888 A1 | 1/2005 | Sherwood et al. | |
| 2006/0017089 A1 | 1/2006 | Taller et al. | |
| 2006/0018083 A1 | 1/2006 | Schmidt | |
| 2006/0035152 A1 | 2/2006 | Nishimura et al. | |
| 2006/0139580 A1 | 6/2006 | Conner et al. | |
| 2006/0139850 A1 | 6/2006 | Rorvick et al. | |
| 2006/0166088 A1 | 7/2006 | Hokanson et al. | |
| 2006/0174463 A1 | 8/2006 | O'Phelan et al. | |
| 2006/0249774 A1 | 11/2006 | Sherwood | |
| 2007/0109723 A1 | 5/2007 | Kuriyama et al. | |
| 2007/0188980 A1 | 8/2007 | Hossick-Schott | |
| 2008/0030927 A1 * | 2/2008 | Sherwood | 361/520 |
| 2008/0170354 A1 | 7/2008 | Dvorak et al. | |
| 2008/0198534 A1 | 8/2008 | Lee et al. | |
| 2008/0208270 A1 | 8/2008 | Linder et al. | |
| 2009/0231782 A1 | 9/2009 | Fujita et al. | |
| 2009/0237862 A1 | 9/2009 | Nielsen et al. | |
| 2009/0242415 A1 | 10/2009 | Yoshimitsu | |
| 2009/0273884 A1 | 11/2009 | Shimizu et al. | |
| 2010/0010562 A1 * | 1/2010 | Daley et al. | 607/37 |
| 2010/0110614 A1 | 5/2010 | Umemoto et al. | |
| 2010/0110615 A1 | 5/2010 | Nishimura et al. | |
| 2010/0157510 A1 | 6/2010 | Miyachi et al. | |
| 2010/0193731 A1 | 8/2010 | Lee et al. | |
| 2010/0195261 A1 | 8/2010 | Sweeney et al. | |
| 2010/0226066 A1 | 9/2010 | Sweeney et al. | |
| 2010/0226070 A1 | 9/2010 | Yang et al. | |
| 2011/0038098 A1 | 2/2011 | Taira et al. | |
| 2011/0149474 A1 | 6/2011 | Sherwood et al. | |
| 2011/0149475 A1 | 6/2011 | Sherwood et al. | |
| 2011/0152959 A1 | 6/2011 | Sherwood et al. | |
| 2011/0152960 A1 | 6/2011 | Daley et al. | |
| 2011/0152961 A1 | 6/2011 | Sherwood | |
| 2013/0141842 A1 | 6/2013 | Sherwood et al. | |
| 2015/0043130 A1 | 2/2015 | Sherwood et al. | |

FOREIGN PATENT DOCUMENTS

| | | |
|---|---|---|
| JP | 2003522420 A | 7/2013 |
| WO | WO-2006139850 A1 | 6/2006 |
| WO | WO-2011075506 A2 | 6/2011 |
| WO | WO-2011075506 A3 | 6/2011 |
| WO | WO-2011075508 A2 | 6/2011 |
| WO | WO-2011075508 A3 | 6/2011 |
| WO | WO-2011075511 A2 | 6/2011 |
| WO | WO-2011075511 A3 | 6/2011 |

OTHER PUBLICATIONS

"U.S. Appl. No. 12/968,536, Non Final Office Action mailed Jun. 21, 2013", 7 pgs.

"U.S. Appl. No. 12/968,555, Notice of Allowance mailed Apr. 2, 2013", 9 pgs.

"U.S. Appl. No. 12/968,555, Notice of Allowance mailed Aug. 28, 2013", 8 pgs.

"U.S. Appl. No. 12/968,555, Notice of Allowance mailed Nov. 23, 2012", 9 pgs.

"U.S. Appl. No. 12/968,555, Response filed Oct. 29, 2012 to Restriction Requirement mailed Sep. 27, 2012", 7 pgs.

"U.S. Appl. No. 12/968,555, Restriction Requirement mailed Sep. 27, 2012", 7 pgs.

"U.S. Appl. No. 12/968,555, Supplemental Notice of Allowability mailed Dec. 26, 2012", 2 pgs.

"U.S. Appl. No. 12/968,561, Response filed Jul. 31, 2013 to Restriction Requirement mailed Jun. 21, 2013", 7 pgs.

"U.S. Appl. No. 12/968,561, Restriction Requirement mailed Jun. 21, 2013", 6 pgs.

"U.S. Appl. No. 12/968,561, Restriction Requirement mailed Aug. 29, 2013", 7 pgs.

"U.S. Appl. No. 12/968,571, Response filed Apr. 3, 2013 to Non Final Office Action mailed Nov. 9, 2012", 13 pgs.

"U.S. Appl. No. 12/968,571, Advisory Action mailed Aug. 22, 2013", 3 pgs.

"U.S. Appl. No. 12/968,571, Final Office Action mailed Jun. 3, 2013", 14 pgs.

(56) References Cited

OTHER PUBLICATIONS

"U.S. Appl. No. 12/968,571, Non Final Office Action mailed Sep. 13, 2013", 15 pgs.
"U.S. Appl. No. 12/968,571, Non Final Office Action mailed Nov. 9, 2012", 15 pgs.
"U.S. Appl. No. 12/968,571, Response filed Jul. 31, 2013 to Final Office Action mailed Jun. 3, 2013", 11 pgs.
"U.S. Appl. No. 12/968,584, Non Final Office Action mailed Jan. 30, 2013", 11 pgs.
"U.S. Appl. No. 12/968,584, Non Final Office Action mailed Jul. 31, 2013", 12 pgs.
"U.S. Appl. No. 12/968,584, Response filed Apr. 26, 2013 to Non Final Office Action mailed Jan. 30, 2013", 10 pgs.
"International Application Serial No. PCT/US2010/060432, Corrected International Preliminary Report on Patentability mailed May 11, 2012", 22 pgs.
"International Application Serial No. PCT/US2010/060432, International Preliminary Report on Patentability mailed Apr. 27, 2012", 16 pgs.
"International Application Serial No. PCT/US2010/060432, Invitation to Pay Additional Fees mailed Sep. 13, 2011", 9 pgs.
"International Application Serial No. PCT/US2010/060432, Search Report mailed Dec. 5, 2011", 6 pgs.
"International Application Serial No. PCT/US2010/060432, Written Opinion mailed Dec. 5, 2011", 14 pgs.
"International Application Serial No. PCT/US2010/060437, International Preliminary Report on Patentability", 7 pgs.
"International Application Serial No. PCT/US2010/060437, Search Report mailed Sep. 13, 2011", 4 pgs.
"International Application Serial No. PCT/US2010/060437, Written Opinion mailed Sep. 13, 2011", 6 pgs.
"International Application Serial No. PCT/US2010/060444, International Preliminary Report on Patentability mailed Jun. 28, 2012", 8 pgs.
"International Application Serial No. PCT/US2010/060444, International Search Report mailed Sep. 14, 2011", 4 pgs.
"International Application Serial No. PCT/US2011/060444, Written Opinion mailed Sep. 14, 2011", 7 pgs.
"U.S. Appl. No. 12/968,536, Response filed Sep. 23, 2013 to Non Final Office Action mailed Jun. 21, 2013", 7 pgs.
"U.S. Appl. No. 12/968,536, Non Final Office Action mailed Oct. 2, 2013", 17 pgs.
"U.S. Appl. No. 12/968,536, Response filed Jan. 2, 2014 to Non-Final Office Action mailed Oct. 2, 2013", 10 pgs.
"U.S. Appl. No. 12/968,561, Notice of Allowance mailed Nov. 13, 2013", 11 pgs.
"U.S. Appl. No. 12/968,561, Response filed Sep. 30, 2013 to Restriction Requirement mailed Aug. 29, 2013", 7 pgs.
"U.S. Appl. No. 12/968,584 , Response filed Oct. 29, 2013 to Non Final Office Action nailed Jul. 31, 2013", 10 pgs.
"U.S. Appl. No. 12/968,584, Notice of Allowance mailed Dec. 27, 2013", 7 pgs.
"Japanese Application Serial No. 2012-544737, Office Action mailed Nov. 5, 2013", With English Translation, 6 pgs.
"U.S. Appl. No. 12/968,536, Advisory Action mailed Sep. 19, 2014", 3 pgs.
"U.S. Appl. No. 12/968,536, Final Office Action mailed Jun. 19, 2014", 9 pgs.
"U.S. Appl. No. 12/968,536, Response filed Aug. 18, 2014 to Final Office Action mailed Jun. 19, 2014", 8 pgs.
"U.S. Appl. No. 12/968,571, Advisory Action mailed Jun. 3, 2014", 3 pgs.
1 "U.S. Appl. No. 12/968,571, Final Office Action mailed Mar. 11, 2014", 15 pgs.
"U.S. Appl. No. 12/968,571, Notice of Allowance mailed Jun. 10, 2014", 7 pgs.
"U.S. Appl. No. 12/968,571, Response filed May 12, 2014 to Final Office Action mailed Mar. 11, 2014", 9 pgs.
"U.S. Appl. No. 12/968,571, Response filed Jun. 10, 2014 to Final Office Action mailed Mar. 11, 2014", 6 pgs.
"U.S. Appl. No. 13/753,023, Non Final Office Action mailed Jul. 24, 2014", 8 pgs.
"U.S. Appl. No. 12/968,536, Non Final Office Action mailed Jan. 16, 2015", 9 pgs.
"U.S. Appl. No. 12/968,561, Non Final Office Action mailed Nov. 17, 2014", 8 pgs.
"U.S. Appl. No. 12/968,561, Response filed Feb. 12, 2015 to Non Final Office Action mailed Nov. 17, 2014", 9 pgs.
"U.S. Appl. No. 13/753,023, Notice of Allowance mailed Nov. 21, 2014", 7 pgs.
"U.S. Appl. No. 14/521,660, Preliminary Amendment filed Nov. 18, 2014", 6 pgs.
"U.S. Appl. No. 13/753,023, Response filed Oct. 22, 2014 to Non Final Office Action mailed Jul. 24, 2014", 8 pgs.
US 8,503,164, 08/2013, Sherwood et al. (withdrawn)

* cited by examiner

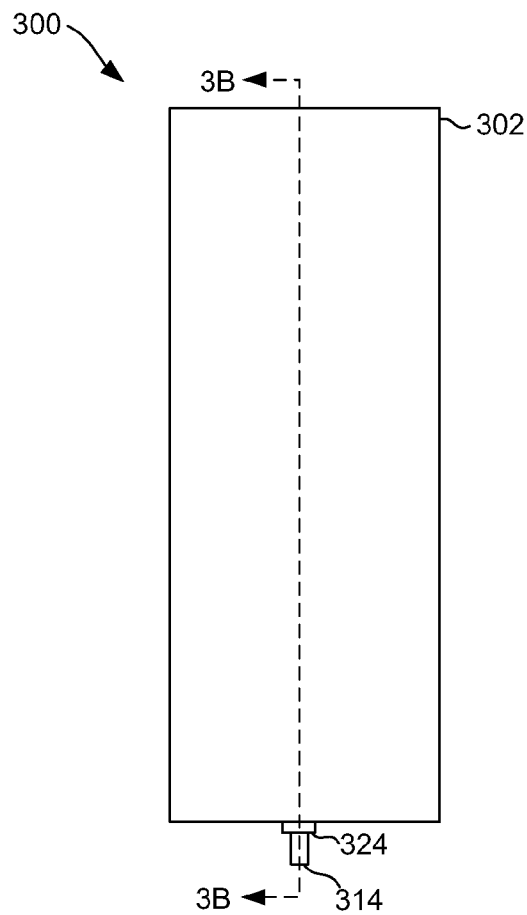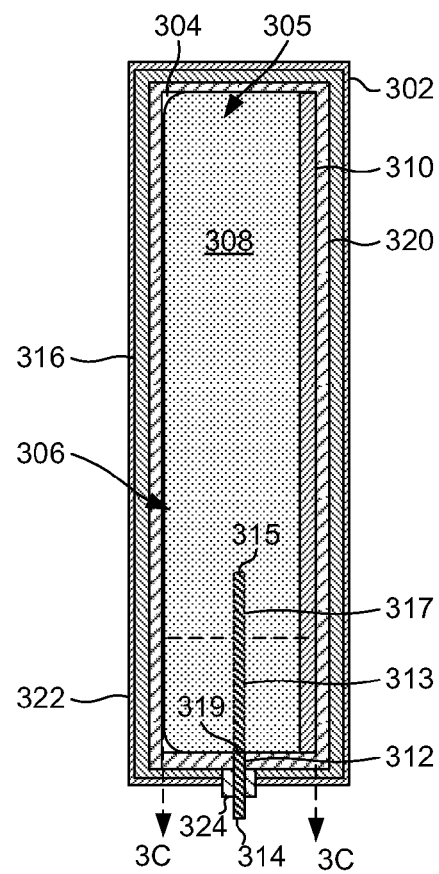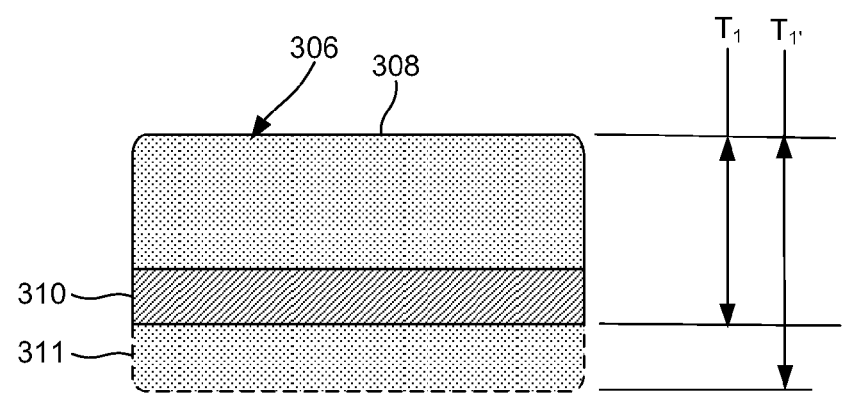

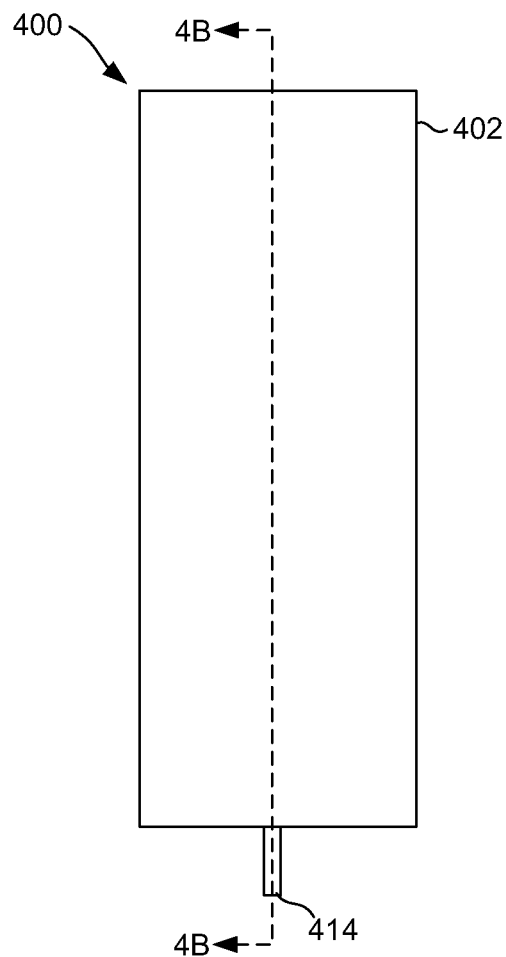
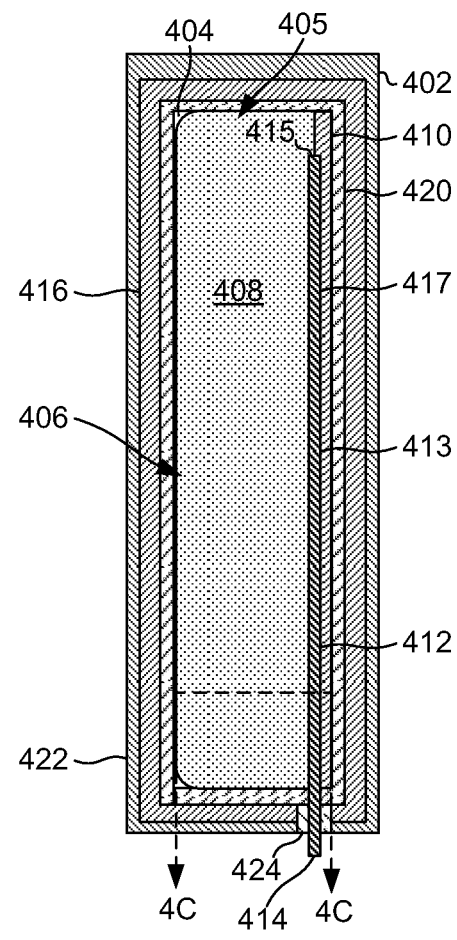
FIG. 4A
FIG. 4B
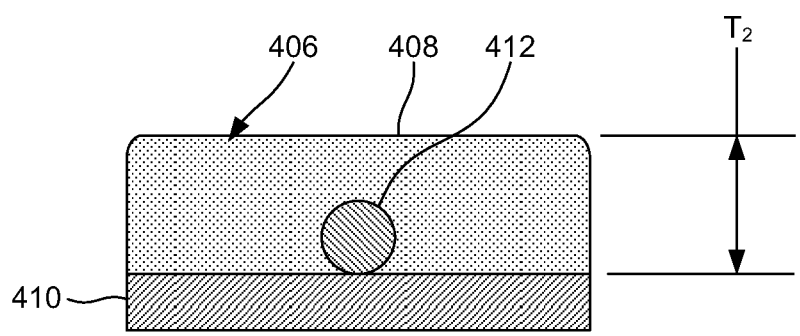
FIG. 4C

SINTERED ELECTRODES TO STORE ENERGY IN AN IMPLANTABLE MEDICAL DEVICE

CROSS-REFERENCE TO RELATED APPLICATIONS

This application claims the benefit of U.S. Provisional Application No. 61/288,062, filed on Dec. 18, 2009, under 35 U.S.C. §119(e), which is incorporated herein by reference in its entirety.

TECHNICAL FIELD

This document relates generally to energy storage and particularly to sintered electrodes to store energy in an implantable medical device.

BACKGROUND

Electrical stimulation therapy has been found to benefit some patients. For example, some patients suffer from an irregular heartbeat or arrhythmia and may benefit from application of electrical stimulation to the heart. Some patients suffer from a particular type of arrhythmia called a fibrillation. Fibrillations may affect different regions of the heart, such as the atria or the ventricles. When a fibrillation occurs in the ventricles, the heart's ability to pump blood is dramatically reduced, putting the patient at risk of harm. It has been found that applying an electrical stimulation to the patient can effectively treat patients suffering disorders such as from fibrillation by restoring a regular heartbeat.

Because disorders such as fibrillations can happen at any time, it is helpful to have a device that is easily accessible to treat them. In some cases, it is helpful if that device is portable or implantable. In developing a device that is portable or implantable, it is helpful to have access to subcomponents that are compact and lightweight and that can perform to desired specifications.

SUMMARY

This document discloses apparatus and methods related to energy storage devices, including energy storage devices for implantable medical devices. One embodiment provides an apparatus including an electrode disposed in a capacitor case, wherein the electrode includes a sintered portion disposed on a substrate. A conductor is coupled to the electrode and extends through the case to a terminal disposed on the exterior of the case. The apparatus includes additional electrodes disposed in the capacitor case, a separator disposed between the electrode and one or more of the additional electrodes, and another terminal in electrical communication with the one or more additional electrodes.

One aspect of the disclosure relates to a method for making a capacitor having a sintered electrode. According to an embodiment of the method an anode material is sintered onto an anode foil, the anode material and the foil are stacked with a cathode into a capacitor case, the anode is coupled to an anode conductor sealed in the capacitor case, the case is filed with electrolyte and sealed. In various embodiments, a system is provided, for example, a system including a cardiac rhythm management circuit coupled to the apparatus.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 3A is a plan view of a capacitor including a slug electrode, according to various embodiments.

FIG. 3B is a cross section taken along line 3B-3B in FIG. 3A.

FIG. 3C is a cross section taken along line 3C-3C in FIG. 3B.

FIG. 4A is a plan view of a capacitor including a slug electrode, with a conductor disposed between a slug and a foil, according to various embodiments.

FIG. 4B is a cross section taken along line 4B-4B in FIG. 4A.

FIG. 4C is a partial cross section taken along line 4C-4C in FIG. 4A, with a case and separator not shown.

DETAILED DESCRIPTION

Figure 1:
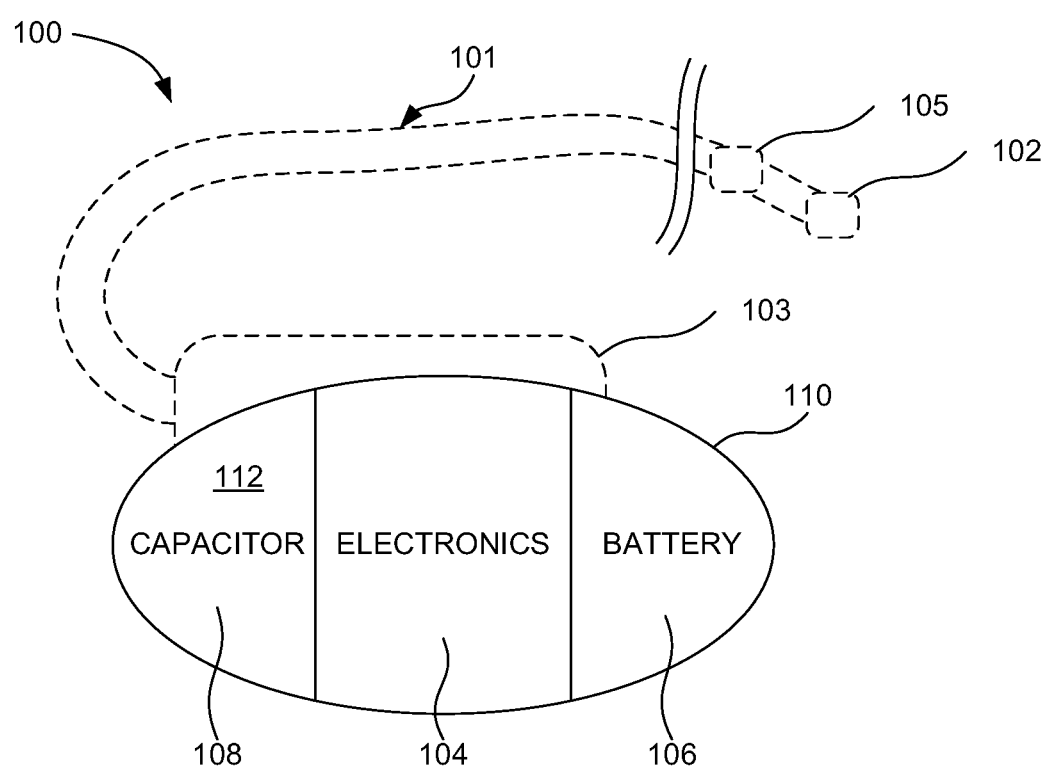
FIG. 1 is a schematic of a medical system including a sintered capacitor, according to some embodiments.

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This document concerns sintered electrodes for use in an electrical energy storage device. Specific examples include sintered anodes formed of aluminum or its alloys. Certain examples are for use in aluminum electrolytic capacitors. Examples include electrodes with a sintered portion disposed onto at least one side of a substrate. Some examples include a stack of electrodes in which the substrates of multiple electrodes are interconnected. This interconnection method improves upon energy storage devices using etched electrodes because the foils may be bent together for interconnection with a low risk of breakage, whereas etched materials often break. Additional benefits stem from an increased surface area that is a product of sintering.

Sintering results in many interstices (i.e., spaces) between grains of the electrode. Sintered electrodes resemble crushed grains with interstices between the grains. The interstices are filled with electrolyte, thereby increasing capacitance per unit of volume, as capacitance is proportional to a surface area exposed to electrolyte. An electrode with such interstices offers improved lateral or parallel movement of electrons in relation to a major surface of a flat electrode layer, as etched electrodes restrict lateral movement because the etchings result in voids that are typically perpendicular to the major surface of the flat layer. Accordingly, some examples have a lower ESR (equivalent series resistance) compared to etched foils due to this enhance ionic flow.

Overall, an energy storage device using the sintered electrodes described here is well suited for use in an implantable medical device such as a defibrillator. Because sintering can produce a variety of shapes, sintered electrodes can be used to create energy storage devices such as capacitors that have custom shapes versus simple cylinders or a prism having a parallelogram as its base. Further, manufacturing efficiency is improved, such as by allowing electrodes to be nested on a web before they are excised from the web and stacked into a capacitor. In other words, nesting reduces waste by allowing more of the web to be converted into electrodes. The interstices are very small, making the electrodes rigid and able to withstand handling by a machine or assembly personnel. These electrodes demonstrate an improved energy density over etched electrodes and are therefore useful to make smaller implantable devices that are able to deliver an amount of energy for a particular therapy.

FIG. 1 is a schematic of a medical system 100 including a sintered capacitor, according to some embodiments. The medical system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

Electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. The electronics 104 can be powered wirelessly using an inductor. Alternatively, the electronics 104 can be powered by a battery 106. In some examples, electronics 104 are to direct small therapeutic bursts of energy to a patient from the battery 106.

For therapies, such as defibrillation, that use energy discharge rates exceeding what battery 106 is able to provide, a capacitor 108 is used. Energy from the battery 106 is controlled by the electronics 104 to charge the capacitor 108. The capacitor 108 is controlled by the electronics 104 to discharge to a patient to treat the patient. In some examples, the capacitor 108 entirely discharges to a patient, and in additional examples, the capacitor is switched on to provide therapeutic energy and switched off to truncate therapy delivery.

Some examples of a medical system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101. Leadless examples can be positioned in contact with the tissue to be stimulated, or can be positioned proximal to tissue to shock the tissue to be stimulated through intermediary tissue. Leadless examples can be easier to implant and can be less expensive as they do not require the additional lead components. The housing 110 can be used as an electrode in leadless configurations.

In certain embodiments, the electronics 104 include an electronic cardiac rhythm management circuit coupled to the battery 106 and the capacitor 108 to discharge the capacitor 108 to provide a therapeutic defibrillation pulse. In some examples, the system 100 includes an anode and a cathode sized to deliver a defibrillation pulse of at least approximately 50 joules. Other configurations can deliver larger amounts of energy. Some configurations deliver less energy. In some examples, the energy level is predetermined to achieve a delivered energy level mandated by a governing body or standard associated with a geographic region, such as a European country. In an additional embodiment, the anode and cathode are sized to deliver a defibrillation pulse of at least approximately 60 joules. In some examples, this is the energy level is predetermined to achieve an energy level mandated by a governing body of another region, such as the United States. In some examples, electronics 104 are to control discharge of a defibrillation pulse so that the medical system 100 delivers only the energy mandated by the region in which the system 100 is used. In some examples, a pulse of 36 joules is delivered.

Packaging anodes and cathodes can reduce their efficiency. Interconnections between conductors coupled to electronics and to the electrodes of the capacitor 108 decrease efficiency, for example. Accordingly, anodes and cathodes are sized to compensate for decreases in efficiency. As such, in some embodiments, the capacitor 108 includes anodes and cathodes sized and packaged to deliver a defibrillation pulse of at least approximately 50 joules. Some are sized and packaged to deliver a defibrillation pulse of at least approximately 60 joules.

One characteristic of some sintered electrode examples is that at least one anode and a cathode have a DC capacitance that is approximately 23% greater than a AC capacitance for the at least one anode and the cathode of an etched capacitor that has 74.5 microfarads per cubic centimeter. In some examples, the at least one anode and the cathode have an AC capacitance of at least 96.7 microfarads per cubic centimeter at 445 total voltage. In some examples, this is comparable to an operating voltage of about 415 volts. This is a 30% improvement over an etched capacitor that has 74.5 microfarads per cubic centimeter. Total voltage is the voltage that allows 1 milliamp of leakage per square centimeter for an electrode. Some examples are aged to 415 volts.

In certain examples, the capacitor 108 includes a capacitor case 112 sealed to retain electrolyte. In some examples, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal.

A hermetically sealed device housing 110 is used to house components, such as the battery 106, the electronics 104, and the capacitor 108. Hermeticity is provided by welding components into the hermetically sealed device housing 110, in some examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The capacitor 108 is improved by the present electrode technology in part because it can be made smaller and with less expense. The improvement provided by these electrodes is pertinent to any application where high-energy, high-voltage, or space-efficient capacitors are desirable, including, but not limited to, capacitors used for photographic flash equipment. The present subject matter extends to energy storage devices that benefit from high surface area sintered electrodes including, but not limited to, aluminum. The electrodes described here can be incorporated into cylindrical capacitors that are wound, in addition to stacked capacitors.

Figure 2:
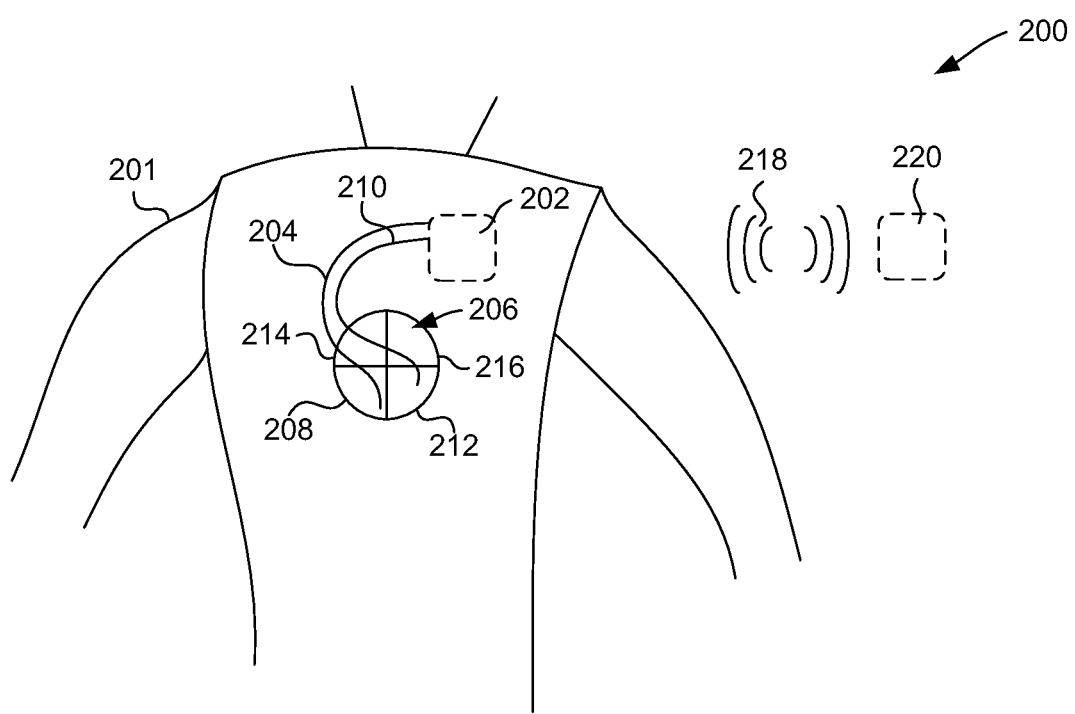
FIG. 2 is an implanted medical system including a sintered capacitor, according to some embodiments.

FIG. 2 is an implanted medical system 200, implanted in a patient 201, and including a sintered capacitor, according to some embodiments. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various embodiments, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both those tissue regions. The second lead 210 is in direct contact with the left atrium 216 and the left ventricle 212 to sense and/or stimulate both those tissue regions. The cardiac rhythm management device 202 uses the lead electrodes to deliver energy to the heart, either between electrodes on the leads or between one or more lead electrodes and the cardiac rhythm management device 202. In some examples, the cardiac rhythm management device 202 is programmable and wirelessly communicates 218 programming information with a programmer 220. In some examples, the programmer 220 wirelessly 218 charges an energy storage device of the cardiac rhythm management device 202.

FIG. 3A is a plan view of a capacitor 300 including a slug electrode 305, according to various embodiments. FIG. 3B is a cross section taken along line 3B-3B in FIG. 3A. FIG. 3C is a cross section taken along line 3C-3C in FIG. 3B. The anode 306 is disposed in a capacitor case 302. The anode 306 includes a sintered portion 308 disposed on a substrate 310. In some examples, the sintered portion 308 is sintered onto the substrate 310. In these examples, grains of the sintered portion 308 are mechanically and electrically coupled to the substrate 310 using the sintering process that forms the sintered portion 308. In some examples, the sintered portion 308 is coupled with the substrate 310 such as through fasteners, adhesion or welding, or combinations thereof. As used herein, fasteners can include rivets, clamps, screws, combinations of these fasteners and other fasteners to mechanically fasten components to one another. Optionally, a second sintered portion 311, may be disposed on a second side of the substrate 310 in addition to the sintered portion 308 disposed on a first side of the substrate 310. In some embodiments, the thickness of the sintered portion 308 is substantially the same as the thickness of the second sintered portion 311. In some embodiments, the thickness of the sintered portion 308 is different from the thickness of the second sintered portion 311. It is understood that electrodes described herein with sintered material disposed on one side of a substrate may also be configured with a substrate having sintered material disposed on two sides of the substrate without departing from the scope of the present subject matter.

As used herein, a slug 305 includes a sintered portion 308 of an anode 306 and any optional substrate 310 to which the sintered portion 308 is mechanically fixed. Some examples include a slug 305, such as a standalone slug, including a monolithic sintered portion 308. In some examples, a slug 305 is standalone in that it is the only slug of a polarity in a capacitor. A sintered portion 308 is monolithic in that it is a solid structure having a regular crystalline or grain structure with no movable subcomponents. An electrode such as anode 306 includes a slug 305 plus any other portions in electrical communication with the slug 305, including, but not limited to, interconnects and/or conductors such as anode conductor 312. For instance, the anode conductor 312 forms some portion of the anode 306, albeit contributing a relatively small amount of capacitance when compared with the slug 305.

In some examples, the substrate 310 is an aluminum foil. Aluminum foil has a thickness of less than 0.008 inches/0.2 mm in various examples. Some aluminum foils are less than or equal to 0.005 inches thick. These foils are easily bent by hand and are easily torn by hand. Substrates that are thicker are additionally possible.

An anode conductor 312 is coupled with one or both the sintered portion 308 and the substrate 310. The anode conductor 312 sealingly extends through the capacitor case 302 to an anode terminal 314 disposed on the exterior of the capacitor case 302, with the anode terminal 314 in electrical communication with the sintered portion 308. Some examples use a feedthrough 324. In some examples, the feedthrough includes glass. In some embodiments, the feedthrough includes epoxy. In some examples, an internal length 313 of the anode conductor 312 is disposed in the sintered portion 309 of the anode 306, with the sintered portion 308 enveloping the internal length 313. In some of these embodiments, the anode 306 is sintered to and around the internal length 313, including being sintered to an end 315 of the internal length 313 and to a side 317 of the internal length 313.

In some examples, the slug is a polyhedron and the anode conductor extends through a face of the anode 306, substantially perpendicular to a face of the anode 306. Some examples include an anode 306 having a polyhedron shape with rounded edges. Anodes 306 having a curved surface or a curvilinear surface are also contemplated. In various embodiments, the anode 306 is from around 300 micrometers to around 400 micrometers in thickness $T_1$ (optionally $T_r$), but the present subject matter is not so limited.

In additional embodiments, the anode conductor 312 is affixed to the side of a slug. These embodiments do not include the internal length 317. In some of these embodiments, an end face 319 of the anode conductor is coupled to the slug. The end face 319 can be sintered or affixed another way, such as by welding, adhesion or fasteners, or combinations thereof.

Alternative examples include an anode conductor 312 coupled to the substrate 310, with the anode conductor 312 in electrical communication with the sintered portion 308 without being in mechanical contact with the sintered portion 308. Various coupling methods are used to join the anode conductor 312 to the substrate 310 including, but not limited to, welding, adhesion, fasteners, and combinations thereof.

Several materials can be used to form case 302, including, but not limited to, aluminum, titanium, stainless steel, nickel, a polymeric material, or combinations of these materials. The case 302 is sealed to retain electrolyte 304. Various electrolytes can be used including, but not limited to, Suzuki-Techno Corporation electrolyte model 1184. The case 302 includes a seal, such as a resin based seal including but not limited to epoxy, in some examples. Some examples include a rubber seal to seal case portions to one another, or to seal subcomponents such as a feedthrough to one or more case portion. In some examples, case 302 is welded together from subcomponents. In certain examples, the case 302 is hermetically sealed. Some examples include a case that includes one or more backfill ports, but the present subject matter is not so limited.

A cathode 316 is also disposed in the capacitor case 302. In some examples, the cathode 316 is a flat layer. Some of these examples are approximately 20 micrometers in thickness. In some examples, the case 302 is cathodic and is part of the cathode 316. In additional embodiments, the case 302 is not cathodic, and the cathode is electrically isolated from the case or the case is not conductive. Material of the cathode 316 can be disposed onto the case using a coating process or another process including, but not limited to, sintering, or it can be disposed against the case without being mechanically coupled to the case. In various embodiments a separator 320 is disposed between the cathode 316 and the sintered portion 308 and substrate 310 of the anode 306. The separator 320 comprises one or more layers of Kraft paper in certain examples. In various examples, a hole is cut in the separator 320 to provide a port for the anode conductor 312. The separator 320 and cathode 316 are illustrated as enveloping the slug 305 (that is, bending or formed around the slug 305), but in some embodiments they comprise flat layers that support the slug 305 on its sides. Some examples include a cathode terminal 322 disposed on an exterior of the capacitor case 302 and in electrical communication with the cathode 316, with the anode terminal 314 and the cathode terminal 322 electrically isolated from one another.

FIG. 4A is a plan view of a capacitor 400 including a slug electrode, with a conductor disposed between a slug and a foil, according to various embodiments. FIG. 4B is a cross section taken along line 4B-4B in FIG. 4A. FIG. 4C is a partial cross section taken along line 4C-4C in FIG. 4A, with a case and separator not shown. An anode 406 is disposed in a capacitor case 402. The anode 406 includes a sintered portion 408 disposed on a substrate 410, and in some examples, the sintered portion 408 is sintered onto the substrate 410. In some examples, the sintered portion 408 is coupled with the substrate 410 such as through adhesion, welding, fasteners, and combinations thereof.

A slug 405 includes a sintered portion 408 of an anode 406 and substrate 410 to which the sintered portion 408 is mechanically coupled. Some examples include a slug 405, such as a standalone slug, including a monolithic sintered portion 408. An anode conductor 412 is sandwiched between the sintered portion 408 and the substrate 410. The anode conductor 412 sealingly extends through the capacitor case 402 to an anode terminal 414 disposed on the exterior of the capacitor case 402, with the anode terminal 414 in electrical communication with the sintered portion 408. Some examples use a feedthrough 424. In some examples, the feedthrough includes glass. In some embodiments, the feedthrough includes epoxy. The sintered portion 408 and the substrate 410 envelope an internal length 413. In some of these embodiments, the anode 406 is sintered to the internal length 413, including being sintered to an end 415 of the internal length 413 and to a side 417 of the internal length 413. In additional embodiments, adhesion, welding, fasteners, or combinations thereof, mechanically couple the anode conductor 412 to one or both of the sintered portion 408 and the substrate 410.

A cathode 416 is also disposed in the capacitor case 402. In some examples, the case 402 is cathodic and is part of the cathode 416. In additional embodiments, the case 402 is not cathodic, and the cathode is electrically isolated from the case or the case is not conductive. The separator 420 and cathode 416 are illustrated as enveloping the slug 405 (that is, bending or formed around the slug 405), but in some embodiments they comprise flat layers that support the slug 405 on its sides. Material of the cathode 416 can be disposed onto the case using a coating process or another process including, but not limited to sintering, or it can be disposed against the case without being mechanically coupled to the case. In various embodiments a separator 420 is disposed between the cathode 416 and the sintered portion 408 and substrate 410 of the anode 406. The separator 420 comprises one or more layers of Kraft paper in some instances. Some examples include a cathode terminal 422 disposed on an exterior of the capacitor case 402 and in electrical communication with the cathode 416, with the anode terminal 414 and the cathode terminal 422 electrically isolated from one another. Electrolyte is disposed in spaces 404.

Although the anode conductor 412 is shown disposed and enveloped primarily by the sintered portion 408, with a tangential point of contact between the anode conductor and the substrate 410, it can be less enveloped by the sintered portion 408. Additionally possible are spaces between the anode conductor 412 and one or both of the sintered portion 408 and the substrate 410.

Figure 5A:
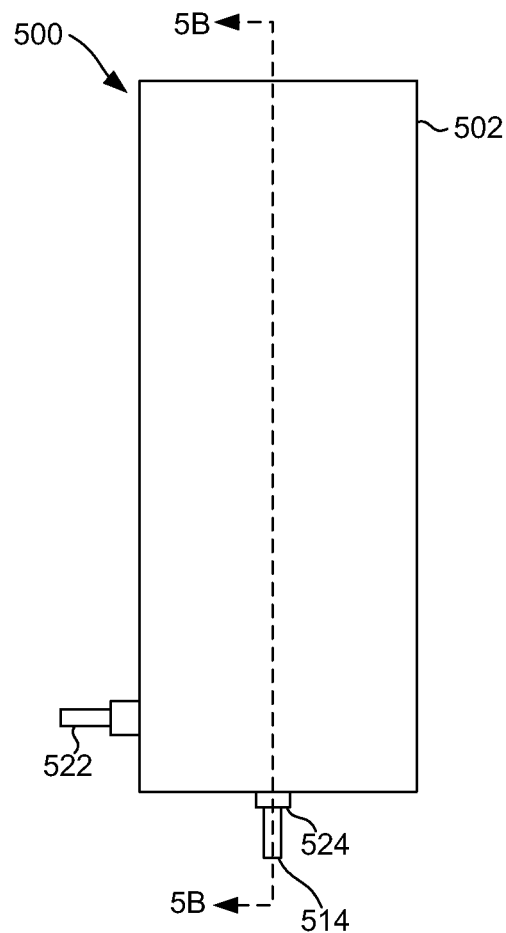
FIG. 5A is a plan view of a capacitor with a sintered portion disposed on an interior of the case, according to various embodiments.
Figure 5B:
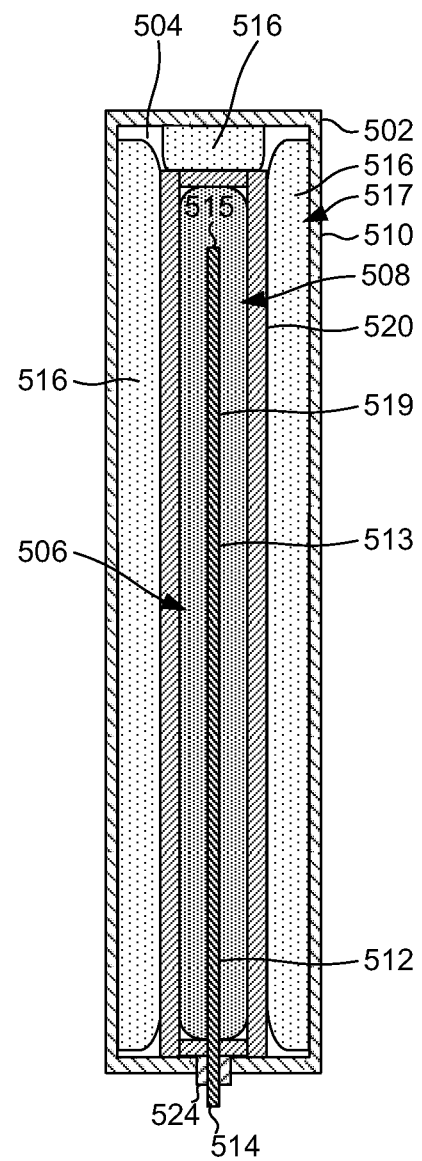
FIG. 5B is a cross section taken along line 5B-5B in FIG. 5A.

FIG. 5A is a plan view of a capacitor 500 with a sintered portion disposed on an interior of the case, according to various embodiments. FIG. 5B is a cross section taken along line 5B-5B in FIG. 5A. An anode 506 is disposed in a capacitor case 502. The anode 506 includes a sintered portion or slug 508 enveloping an anode conductor 512, such as through sintering, welding, adhesion, fasteners, or combinations thereof. Some examples include a slug 505, such as a standalone slug, including a monolithic slug 508. The anode conductor 512 sealingly extends through the capacitor case 502 to an anode terminal 514 disposed on the exterior of the capacitor case 502, with the anode terminal 514 in electrical communication with the sintered portion 508. Some examples use a feedthrough 524. In some examples, the feedthrough includes glass. In some embodiments, the feedthrough includes epoxy. Some embodiments include a feedthrough that includes rubber. Combinations of seals are additionally possible. The sintered portion 508 and the substrate 510 envelope an internal length 513. In some of these embodiments, the anode 506 is sintered to the internal length 513, including being sintered to an end 515 of the internal length 513 and to a side 519 of the internal length 513.

A cathode 517 is disposed on the capacitor case 502 and includes a sintered portion 516. In some examples, the sintered portion 516 is sintered onto the case 502. In additional embodiments, the sintered portion is positioned adjacent or abutting the case 502 in electrical communication with the case 502. In some examples, the sintered portion is mechanically coupled to the case in a manner other than sintering, including, but not limited to, welding, adhesion, fasteners, or combinations thereof. The case 502 is cathodic and is part of the cathode 517. In various embodiments, a separator 520 is disposed between the cathode 517 and the sintered portion 508 and substrate 510 of the anode 506. The separator 520 comprises one or more layers of Kraft paper in some instances. Some examples include a cathode terminal 522 disposed on an exterior of the capacitor case 502 and in electrical communication with the cathode 516, with the anode terminal 514 and the cathode terminal 522 electrically isolated from one another. To aid in assembly, some embodiments adhere or fix the separator 520 to the slug 505 such as with a band or an adhesive, so long as ionic transfer through the electrolyte is possible.

Figure 6A:
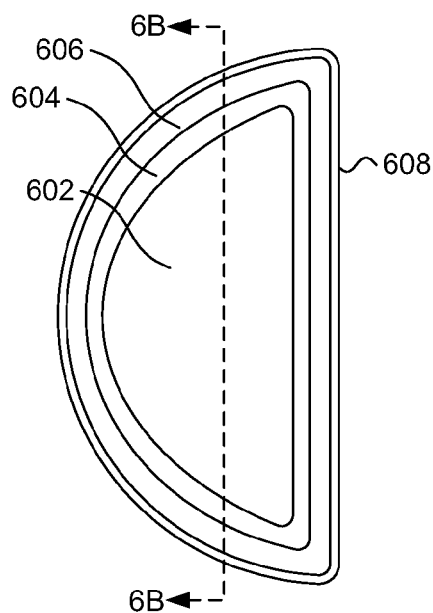
FIG. 6A is a plan view of an electrode, substrate, and a separator, according to various embodiments.
Figure 6B:
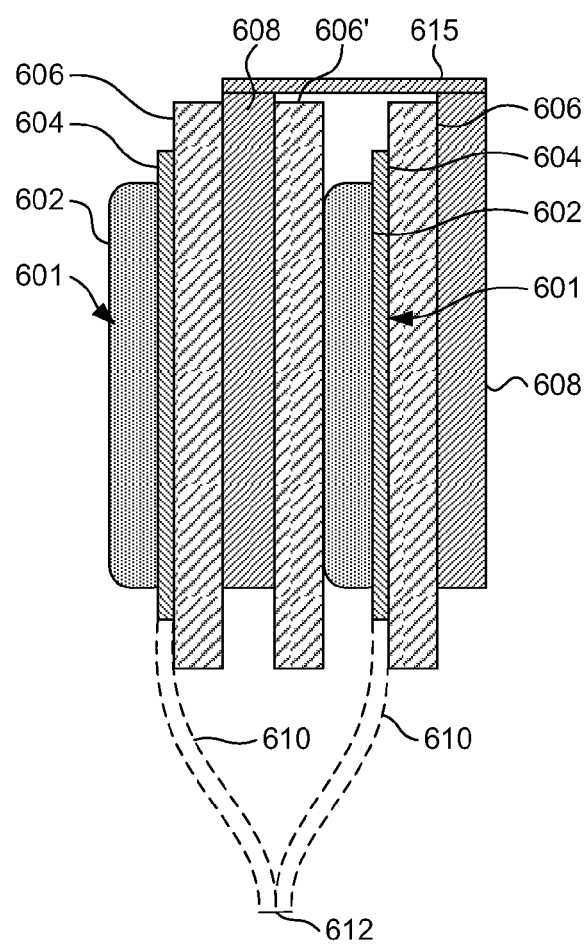
FIG. 6B is a cross section taken along the line 6B-6B in FIG. 6A, illustrating additional separators, an additional electrode and an additional substrate, according to various embodiments.

FIG. 6A is a plan view of an electrode, substrate, and a separator. FIG. 6B is a cross section taken along the line 6B-6B in FIG. 6A, illustrating additional separators, an additional electrode, and an additional substrate, according to various embodiments. The example illustrates two elements 614. A plurality of anodes 601 are illustrated, each including a sintered portion 602 disposed on a respective substrate 604. Each element includes an anode 601 separated from a cathode 608 with separator 606. The elements can be stacked onto one another to provide a range of energy storage capabilities. This ability allows a manufacturer to produce capacitors for a variety of therapies using common parts. In various examples, a separator 606' separates elements electrically and mechanically.

After a stack of elements is created, some examples interconnect cathodes 608 to one another using an interconnect 615. In some examples, the interconnect 615 is a solid conductive bar welded to multiple electrodes. The anodes are connected via a conductive interconnect in some embodiments, or can optionally be interconnected by interconnecting respective substrates 610. In some examples, the substrates are pressed together to define an edge face 612 along which a conductive bar can be welded or a weld can otherwise be drawn. Welds contemplated include, but are not limited to, laser welds.

Figure 7A:
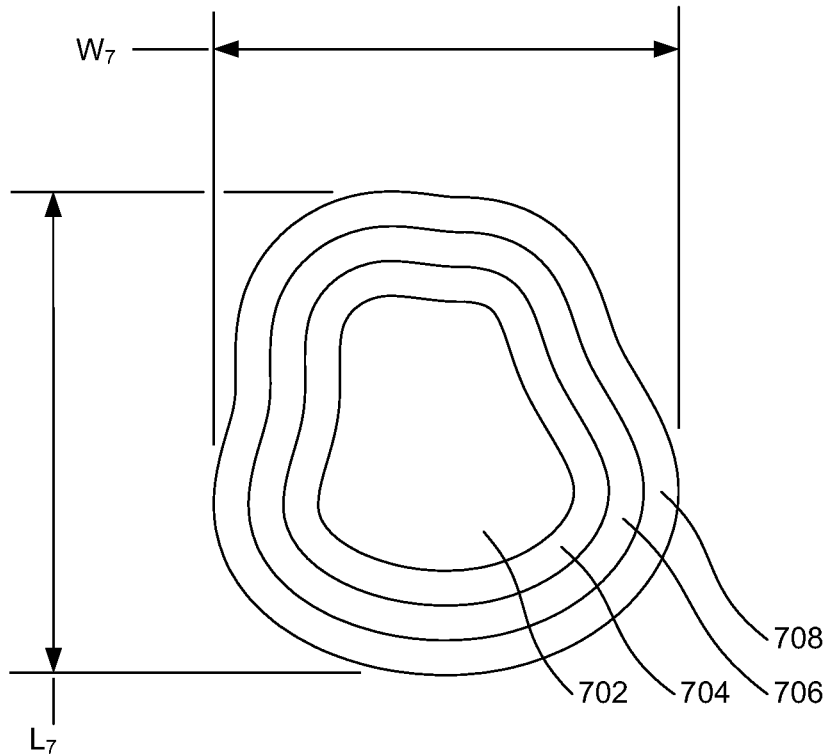
FIG. 7A is a plan view of a stack of electrodes, each including a sintered portion on a substrate, according to various embodiments.
Figure 7B:
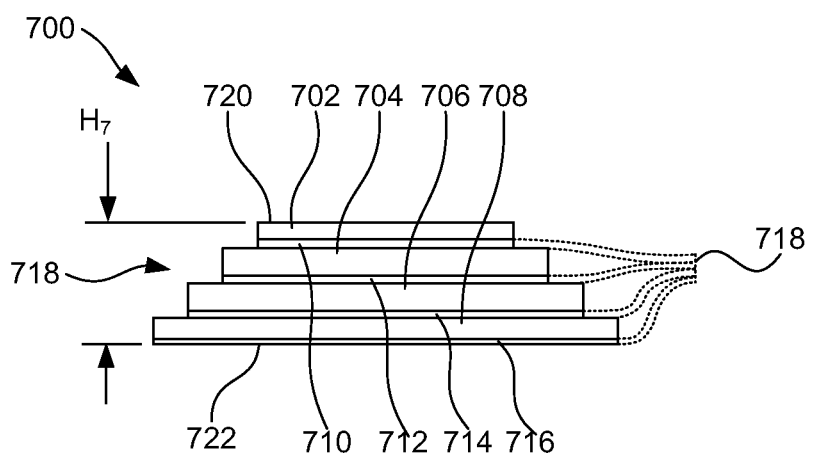
FIG. 7B is a front view of the stack of electrodes of FIG. 7A.

FIG. 7A is a plan view of a stack of electrodes, each including a sintered portion on a substrate, according to various embodiments. FIG. 7B is a front view of the stack of electrodes of FIG. 7A. In some embodiments, the stack 700 is an anode. To increase surface area of an anode, several slugs are positioned against one another and each includes a sintered portion disposed on a substrate. A first slug includes a sintered portion 702 and a substrate 710. A second slug includes a sintered portion 704 and a substrate 712. A third slug includes a sintered portion 706 and a substrate 714. A fourth slug includes a sintered portion 708 and a substrate 716.

In various examples, the slugs are interconnected to one another mechanically and electrically. In some examples, the slugs each abut one another and are electrically connected via the abutment. In some examples, the sintered portions are welded to one another using resistance welding, such as by applying a voltage across several slugs along the axis of stacking. In some examples, several slug layers are interconnected by interconnecting their respective substrates, such as by adhesion, welding, fasteners, or combinations thereof. In some examples, substrates are interconnected to define an edge face 718. Along the edge face, interconnection configurations include, but are not limited to, welding (including, but not limited to, laser welding), adhesion fasteners, and combinations thereof. Additionally, the substrates can be resistance welded together such as by pinching and welding.

In the illustrated configuration, a first sintered portion 702 is sintered onto a first substrate 710, and a second sintered portion 704 is sintered onto a second substrate 712. The first substrate 710 faces the second sintered portion 704 and abuts it. In additional configurations, the second slug is flipped, and the first substrate 710 abuts the second substrate 712.

In the illustrated configuration, the plurality of anodes are stacked to a stack height $H_7$, and at least two of the sintered anodes have respective widths $W_7$, perpendicular to the height $H_7$, that are substantially different such that the plurality of sintered anodes define a contoured edge 718, with the contoured edge 718 extending between a top major face 720 of a top sintered portion 702 and a bottom major face 722 of a bottom substrate 716. Accordingly, the top major face 720 and the bottom major face 722 have different areas. The top major face 720 and the bottom major face 722 are substantially parallel.

In another configuration, the plurality of slugs are stacked to a stack height $H_7$, and at least two of the sintered anodes have respective widths $W_7$, perpendicular to the height $H_7$, that are substantially equal such that the plurality of sintered anodes define a side surface that is substantially parallel to the height $H_7$. In the illustrated configuration, the top major face 720 and the bottom major face 722 are shaped similarly. In additional embodiments, they are not.

Figure 8A:
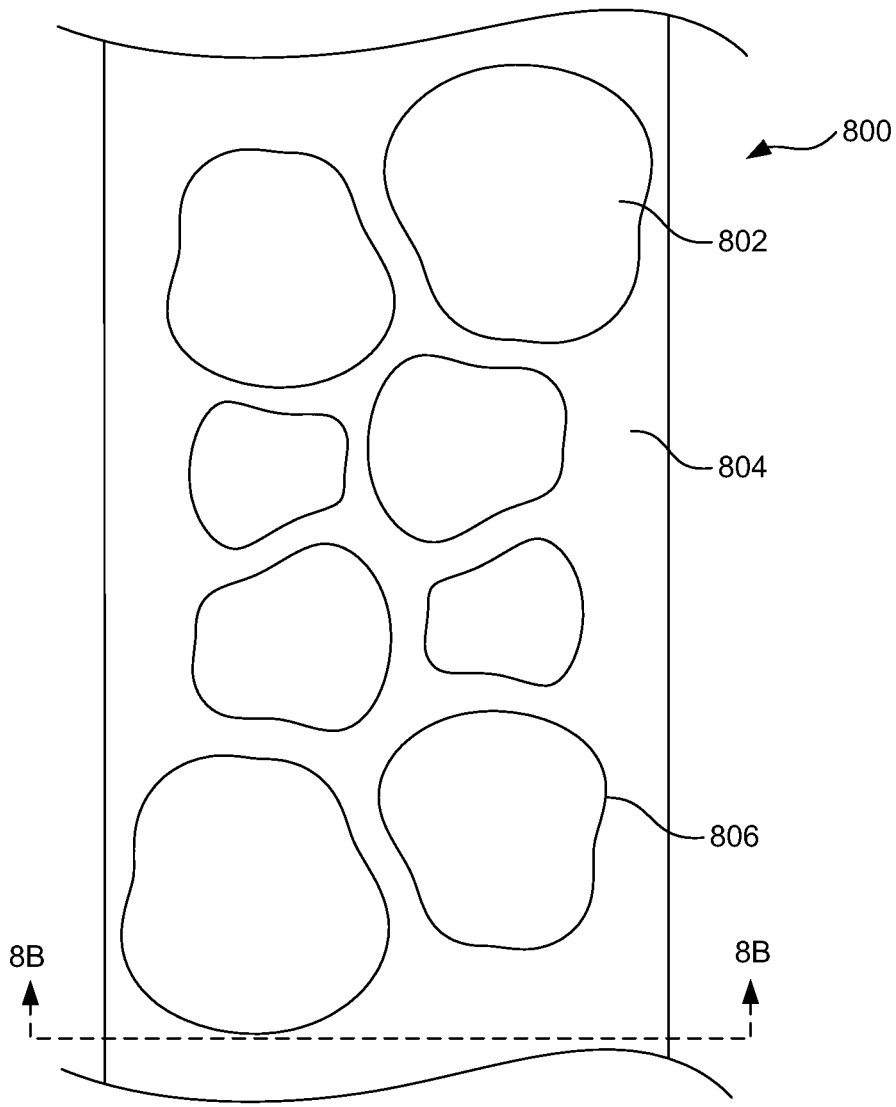
FIG. 8A is a plan view of nested sintered capacitor electrodes that have yet to be excised from a substrate, according to some embodiments.
Figure 8B:
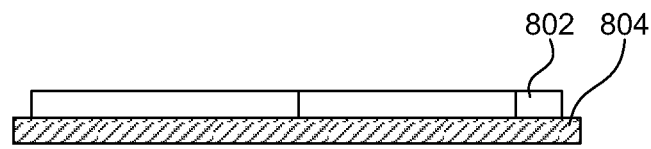
FIG. 8B is a front view of the electrodes and substrate of FIG. 8A.

FIG. 8A is a plan view of nested sintered capacitor electrodes that have yet to be excised from a substrate, according to some embodiments. FIG. 8B is a front view of the electrodes and substrate of FIG. 8A. Electrodes 802 are sintered onto a substrate 804. In various embodiments, the sintered portions are excised from the web 800. In some examples, a slug is cut on the illustrated perimeters, around them, or inside them, depending on the process used. If foils are desired, such as for use as interconnects, one or more slugs are excised around the illustrated perimeters. If no foils are desired, one or more slugs can be excised substantially at the illustrated perimeters such as perimeter 806. In some embodiments, a process cuts the slugs, such as to provide a fresh cut surface or squared edges. FIG. 8B is a front view of the electrodes and substrate of FIG. 8A and illustrates that the slugs are of a common height. The present subject matter is not so limited.

Figure 9:
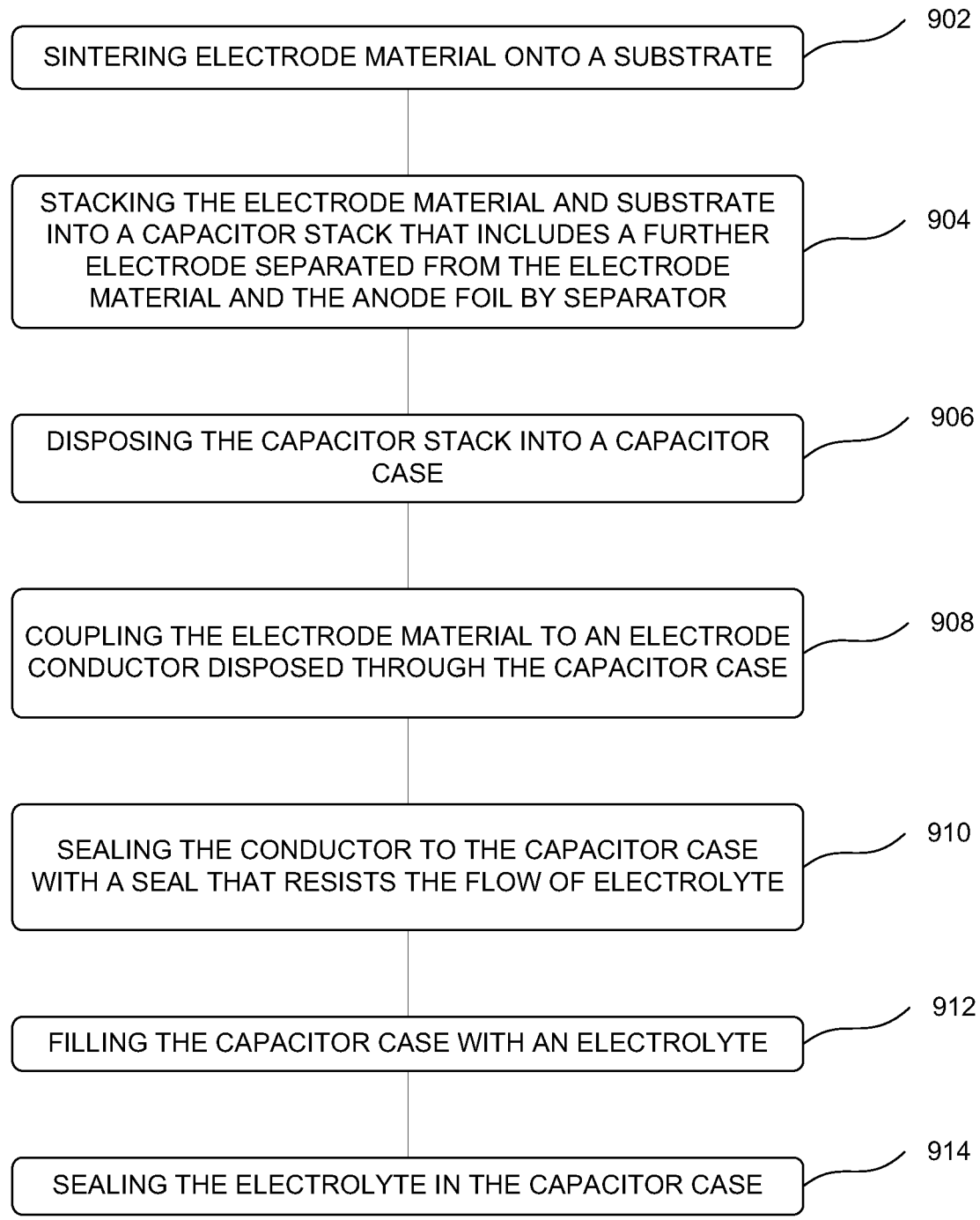
FIG. 9 is a method of making a capacitor, according to some embodiments.

FIG. 9 is a method according to some embodiments. At 902, the method includes sintering electrode material onto an electrode substrate. At 904, the method includes stacking the electrode material and substrate into a capacitor stack that includes a cathode separated from the electrode material and the electrode substrate by separator. At 906, the method includes disposing the capacitor stack into a capacitor case. At 908, the method includes coupling the electrode material to an electrode conductor disposed through the capacitor case. At 910, the method includes sealing the electrode conductor to the capacitor case with a seal that resists the flow of electrolyte. At 912, the method includes filling the capacitor case with electrolyte. At 914, the method includes sealing the electrolyte in the capacitor case.

This application is intended to cover adaptations or variations of the present subject matter. It is to be understood that the above description is intended to be illustrative and not restrictive. The scope of the present subject matter should be determined with reference to the appended claims, along with the full scope of legal equivalents to which such claims are entitled.

What is claimed is:

1. An apparatus, comprising:
a capacitor case sealed to retain electrolyte, the capacitor case inner surface defining a conductive substrate;
a first electrode comprising a plurality of first electrode material portions disposed in the capacitor case, the plurality of first electrode material portions comprising a sintered portion disposed on a second substrate, wherein the plurality of first electrode material portions are disposed onto the second substrate, in a nested configuration, with at least a first first electrode portion having a different area than a second first electrode portion;
a conductor coupled to the second substrate in electrical communication with the sintered portion, the conductor seatingly extending through the capacitor case to a terminal disposed on an exterior of the capacitor case with the terminal in electrical communication with the sintered portion;
a second electrode disposed in the capacitor case, the second electrode comprising a sintered portion disposed on the conductive substrate on the inner surface of the capacitor case;
a separator disposed between the first electrode and the second electrode; and
a second terminal disposed on the exterior of the capacitor case and in electrical communication with the second electrode, with the terminal and the second terminal electrically isolated from one another.

2. The apparatus of claim 1, wherein the first electrode is anodic, and the second electrode is cathodic.

3. The apparatus of claim 1, wherein the at least one electrode and the second electrode have a DC capacitance that is approximately 23% greater than an AC capacitance over an etched capacitor that has a capacitance of 74.5 microfarads per cubic centimeter.

4. The apparatus of claim 3, wherein the AC capacitance is at least 96.7 microfarads per cubic centimeter at 445 total voltage.

5. The apparatus of claim 1, wherein the at least one electrode comprises a standalone slug that includes the sintered portion, with the sintered portion being monolithic.

6. The apparatus of claim 5, wherein the conductor is disposed in the slug, with the slug enveloping a conductive portion of the conductor.

7. The apparatus of claim 5, wherein the conductor is disposed between the slug and the substrate.

8. The apparatus of claim 5, wherein the conductor is disposed outside the slug and is coupled to the slug.

9. A system, comprising:
a hermetically sealed device housing;
a battery disposed in the hermetically sealed device housing;
a capacitor disposed in the hermetically sealed device housing, the capacitor comprising:
a capacitor case sealed to retain electrolyte;
a plurality of anode material portions disposed in the capacitor case, the plurality of anode material portions comprising a sintered portion disposed on a substrate, wherein the plurality of anode material portions are disposed onto the substrate in a nested configuration, with at least a first anode portion having a different area than a second anode portion;
an anode conductor coupled to the substrate in electrical communication with the sintered portion, the anode conductor sealingly extending through the capacitor case to an anode terminal disposed on exterior of the capacitor case with the anode terminal in electrical communication with the sintered portion;
a cathode disposed in the capacitor case;
a separator disposed between the cathode and the anode; and
a cathode terminal disposed on the exterior of the capacitor case and in electrical communication with the cathode, with the anode terminal and the cathode terminal electrically isolated from one another, and
an electronic cardiac rhythm management circuit coupled to the battery and the capacitor and adapted to discharge the capacitor to provide a therapeutic defibrillation pulse.

10. The system of claim 9, wherein the electronic cardiac rhythm management circuit comprises a defibrillator circuit.

11. The system of claim 10, wherein the defibrillator circuit is to discharge the anode and the cathode to provide a single therapeutically effective defibrillator pulse.

12. The system of claim 11, wherein the anode and the cathode are sized to deliver a defibrillation pulse of approximately 36 joules.

13. The system of claim 11, wherein the anode and the cathode are sized and packaged to deliver a defibrillation pulse of approximately 36 joules.

14. A method, comprising:
sintering anode material onto an anode foil; and
sintering a plurality of anode material portions onto the foil in a nested configuration, with at least a first anode portion having a different area than a second anode portion;
stacking the anode material and foil into a capacitor stack that includes a cathode separated from the anode material and the anode foil by a separator;
disposing the capacitor stack into a capacitor case;
coupling the anode material to an anode conductor disposed through the capacitor case;
sealing the anode conductor to the capacitor case with a seal that resists a flow of electrolyte;
filling the capacitor case with an electrolyte; and
sealing the electrolyte in the capacitor case.

15. The method of claim 14, comprising excising each of the plurality of anode material portions from the foil by cutting the foil surrounding at least one of the plurality of anode material portions.

16. The method of claim 14, comprising excising a plurality of anode layers from the sintering on the anode foil.

17. An apparatus, comprising:
a capacitor case sealed to retain electrolyte, the capacitor case inner surface defining a conductive substrate;
a first electrode comprising a sintered portion disposed on the conductive substrate on the inner surface of the capacitor case;
a second electrode disposed in the interior of the capacitor case and disposed against the first electrode, the second electrode separated from the first electrode with a separator that is disposed between the first electrode and the second electrode, wherein the second electrode includes a plurality of second electrode material portions disposed in the capacitor case, the plurality of second electrode material portions comprising a sintered portion disposed on a second substrate, wherein the plurality of second electrode material portions are disposed onto the second substrate in a nested configuration, with at least a first second electrode portion having a different area than a second second electrode portion;

a conductor sealingly disposed through the capacitor case in electrical isolation from the capacitor case, the conductor coupled with the second electrode and with a terminal disposed outside the capacitor case, the terminal in electrical communication with the second electrode; and a second terminal disposed outside the capacitor case in electrical communication with the capacitor case.

18. The apparatus of claim 17, wherein the first electrode is cathodic.

* * * * *